US012589263B2

(12) United States Patent
Chen et al.

(10) Patent No.: US 12,589,263 B2
(45) Date of Patent: Mar. 31, 2026

(54) THERAPEUTIC FOCUSED ULTRASOUND SYSTEMS AND METHODS HAVING TREATMENT BLOCKS THAT ARE ROTATABLE AROUND REFERENCE AXIS FOR INDEPENDENT PHASE AND AMPLITUDE CONTROL

(71) Applicant: SHANGHAI UNITED IMAGING HEALTHCARE CO., LTD., Shanghai (CN)

(72) Inventors: Yujie Chen, Wuhan (CN); Kang Si, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 0 days.

(21) Appl. No.: 18/946,851

(22) Filed: Nov. 13, 2024

(65) Prior Publication Data

US 2025/0213890 A1 Jul. 3, 2025

(30) Foreign Application Priority Data

Dec. 29, 2023 (CN) .......................... 202311862588.7

(51) Int. Cl.
*A61N 7/00* (2006.01)

(52) U.S. Cl.
CPC ........ *A61N 7/00* (2013.01); *A61N 2007/0043* (2013.01); *A61N 2007/0078* (2013.01)

(58) Field of Classification Search
CPC .............. A61N 7/00; A61N 2007/0043; A61N 2007/0078
See application file for complete search history.

(56) References Cited

U.S. PATENT DOCUMENTS

2006/0235300 A1* 10/2006 Weng ................... A61B 8/4461
601/2
2013/0051178 A1* 2/2013 Rybyanets ............. A61B 8/485
367/138

* cited by examiner

*Primary Examiner* — Serkan Akar
(74) *Attorney, Agent, or Firm* — METIS IP LLC

(57) ABSTRACT

A therapeutic ultrasound system may be provided. The therapeutic ultrasound system may comprise a therapeutic ultrasound probe. The therapeutic ultrasound probe may comprise treatment blocks each of which includes one or more ultrasonic transducer arrays. Each of the one or more ultrasonic transducer arrays may include one or more ultrasonic transducers. The treatment blocks may be movable to rotate around a reference axis and/or adjust an angle with respect to the reference axis.

18 Claims, 8 Drawing Sheets

<u>100</u>

500

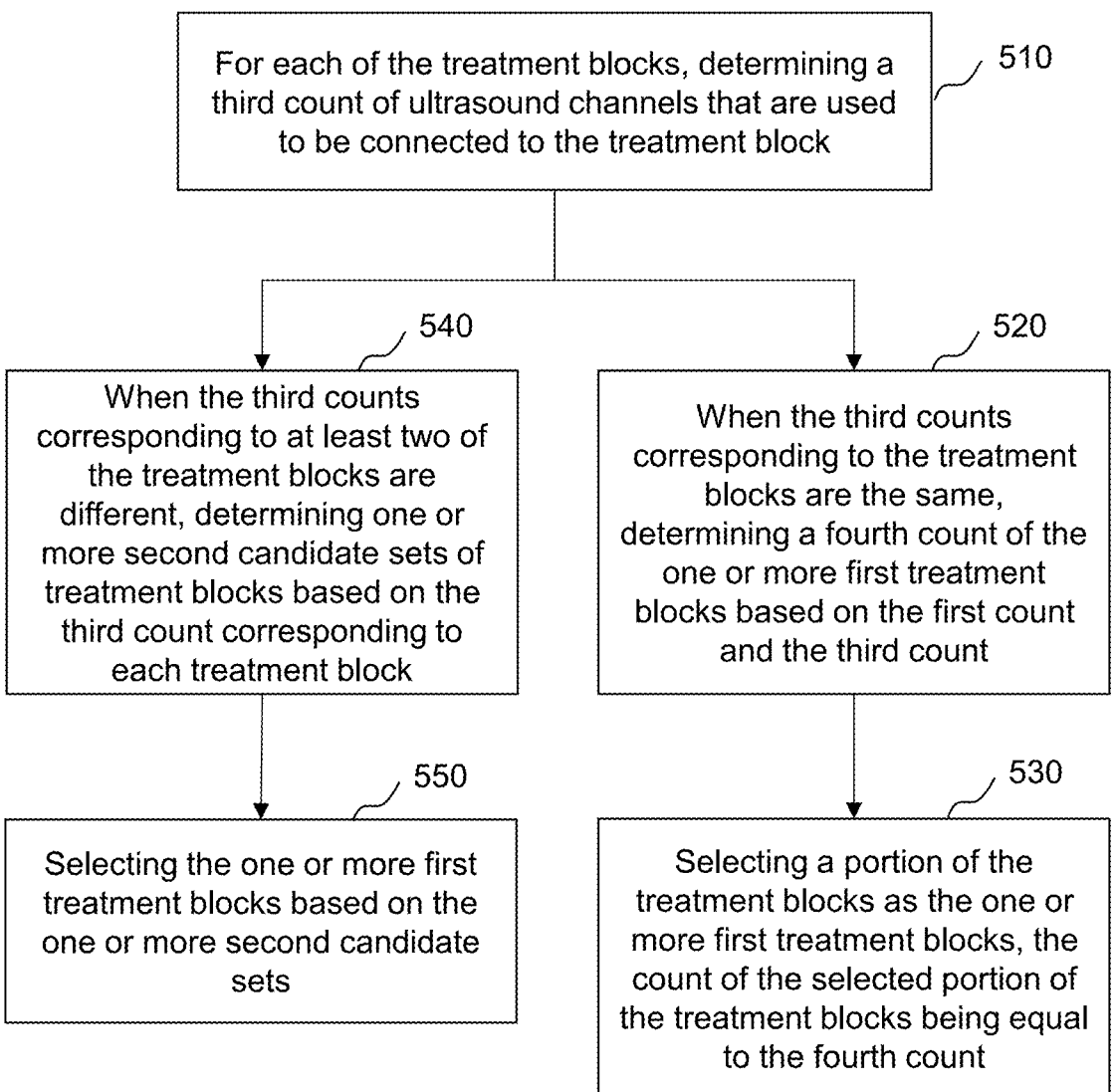

For each of the treatment blocks, determining a third count of ultrasound channels that are used to be connected to the treatment block ⟋ 510

When the third counts corresponding to at least two of the treatment blocks are different, determining one or more second candidate sets of treatment blocks based on the third count corresponding to each treatment block ⟋ 540

When the third counts corresponding to the treatment blocks are the same, determining a fourth count of the one or more first treatment blocks based on the first count and the third count ⟋ 520

Selecting the one or more first treatment blocks based on the one or more second candidate sets ⟋ 550

Selecting a portion of the treatment blocks as the one or more first treatment blocks, the count of the selected portion of the treatment blocks being equal to the fourth count ⟋ 530

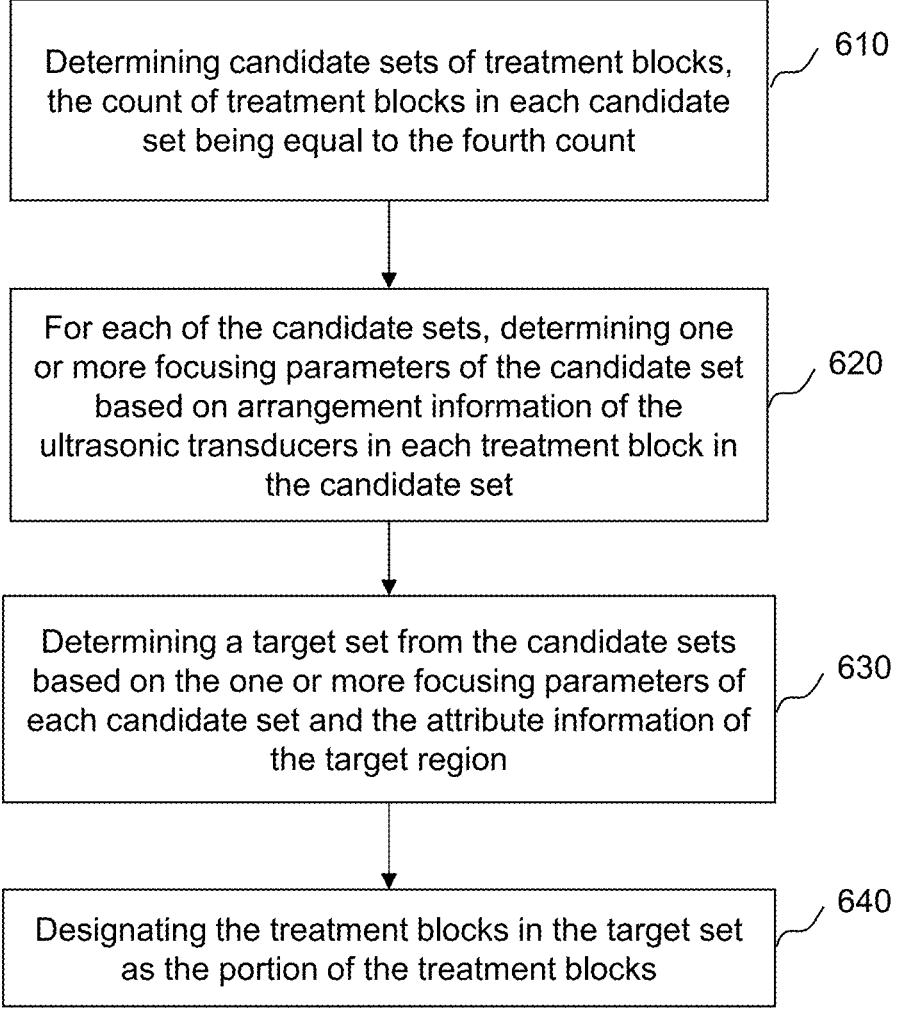

Determining candidate sets of treatment blocks, the count of treatment blocks in each candidate set being equal to the fourth count ⟋ 610

For each of the candidate sets, determining one or more focusing parameters of the candidate set based on arrangement information of the ultrasonic transducers in each treatment block in the candidate set ⟋ 620

Determining a target set from the candidate sets based on the one or more focusing parameters of each candidate set and the attribute information of the target region ⟋ 630

Designating the treatment blocks in the target set as the portion of the treatment blocks ⟋ 640

FIG. 6

700
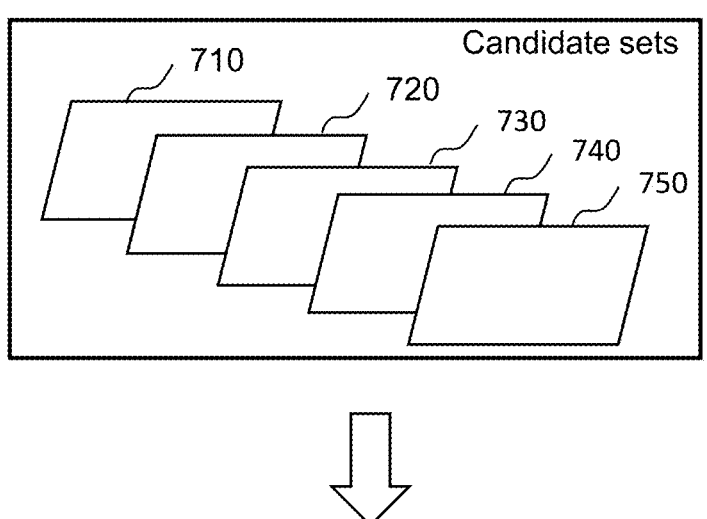
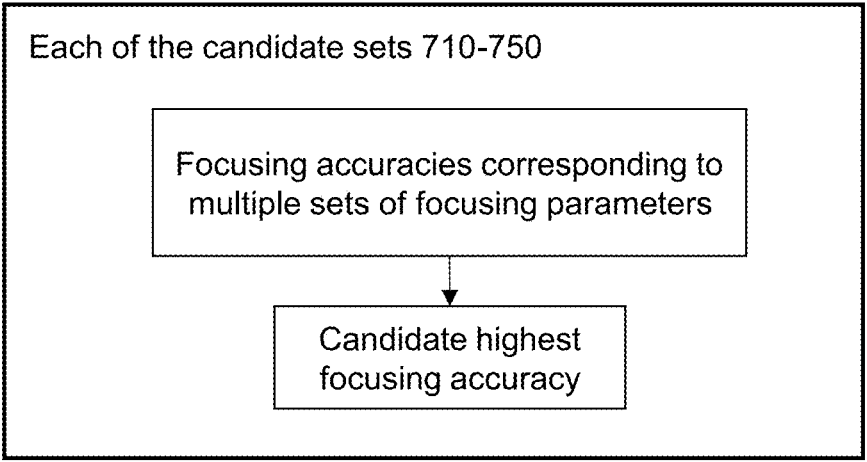
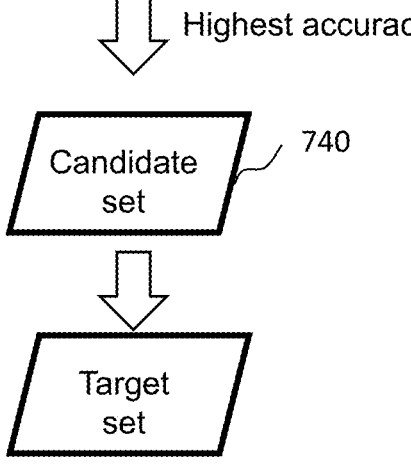
FIG. 7

<u>800</u>

THERAPEUTIC FOCUSED ULTRASOUND SYSTEMS AND METHODS HAVING TREATMENT BLOCKS THAT ARE ROTATABLE AROUND REFERENCE AXIS FOR INDEPENDENT PHASE AND AMPLITUDE CONTROL

CROSS-REFERENCE TO RELATED APPLICATIONS

This application claims priority of Chinese Patent Application No. 202311862588.7, filed on Dec. 29, 2023, the contents of which are incorporated herein by reference.

TECHNICAL FIELD

The present disclosure relates to medical technology field, and in particular, to therapeutic ultrasound systems and methods.

BACKGROUND

The therapeutic ultrasound system is extensively employed for the treatment of internal body structures. Typically, this system utilizes a therapeutic ultrasound probe capable of focusing ultrasonic energy on specific locations within a three-dimensional space, thereby facilitating targeted treatment. For instance, when treating a lesion in a patient's head, the therapeutic ultrasound probe can be equipped with ultrasonic transducer arrays mounted on its inner surface. These ultrasonic transducer arrays have independently adjustable amplitude and phase controls, enabling precise focusing of ultrasonic energy on the targeted lesion within the patient's head to effectively treat the lesion.

SUMMARY

According to an aspect of the present disclosure, a therapeutic ultrasound system may be provided. The therapeutic ultrasound system may comprise a therapeutic ultrasound probe. The therapeutic ultrasound probe may comprise treatment blocks each of which includes one or more ultrasonic transducer arrays. Each of the one or more ultrasonic transducer arrays may include one or more ultrasonic transducers. The treatment blocks may be movable to rotate around a reference axis and/or adjust an angle with respect to the reference axis.

In some embodiments, the treatment blocks are detachable from the therapeutic ultrasound probe.

In some embodiments, the treatment blocks are assembled into the therapeutic ultrasound probe, an inner surface of the therapeutic ultrasound probe is an axisymmetric surface or a portion of the axisymmetric surface, and the reference axis is a symmetry axis of the axisymmetric surface.

In some embodiments, an inner surface of the therapeutic ultrasound probe is a concave surface.

In some embodiments, the treatment blocks are assembled into the therapeutic ultrasound probe, an inner surface of the therapeutic ultrasound probe conforms to the shape of a target body part.

In some embodiments, the therapeutic ultrasound probe is used in combination with a first count of ultrasound channels, one or more first treatment blocks of the therapeutic ultrasound probe are used for a treatment to be performed on a target region of a target subject, a second count is equal to or smaller than the first count, and The second count is a total count of ultrasound channels that are used to be connected to the one or more first treatment blocks.

In some embodiments, one or more second treatment blocks other than the one or more first treatment blocks are removed from the therapeutic ultrasound probe.

In some embodiments, the therapeutic ultrasound system further comprises a processing device. The processing device may be configured to perform the following operations. For each of the treatment blocks, the processing device determines a third count of ultrasound channels that are used to be connected to the treatment block. Further, the processing device selects the one or more first treatment blocks from the treatment blocks based on the first count and the third count corresponding to each of the treatment blocks.

In some embodiments, the third counts corresponding to the treatment blocks are the same, and the processing device is configured to select the one or more first treatment blocks from the treatment blocks by performing the following operations. The processing device determines a fourth count of the one or more first treatment blocks based on the first count and the third count. Further, the processing device selects a portion of the treatment blocks as the one or more first treatment blocks, the count of the selected portion of the treatment blocks being equal to the fourth count.

In some embodiments, the fourth count is determined based on a ratio of the first count to the third count.

In some embodiments, the portion of the treatment blocks are selected from the treatment blocks further based on attribute information of a target region of a target subject to be treated.

In some embodiments, the ultrasonic transducers of different treatment blocks have different arrangements, and the portion of the treatment blocks are selected from the treatment blocks by performing the following operations. The processing device determines candidate sets of treatment blocks, the count of treatment blocks in each candidate set being equal to the fourth count. For each of the candidate sets, the processing device determines one or more focusing parameters of the candidate set based on arrangement information of the ultrasonic transducers in each treatment block in the candidate set. Further, the processing device determines a target set from the candidate sets based on the one or more focusing parameters of each candidate set and the attribute information of the target region. Then, the processing device designates the treatment blocks in the target set as the portion of the treatment blocks.

In some embodiments, the third counts corresponding to at least two of the treatment blocks are different, the processing device is configured to select the one or more first treatment blocks from the treatment blocks by performing the following operations. The processing device determines one or more candidate sets of treatment blocks based on the third count corresponding to each treatment block, wherein a sum of the third counts corresponding to the treatment blocks in each candidate set is smaller than the first count, and a difference between the sum and the first count is not greater than a threshold value. Further, the processing device selects the one or more first treatment blocks based on the one or more candidate sets.

In some embodiments, the one or more candidate sets include multiple candidate sets, to select the one or more first treatment blocks based on the one or more candidate sets, the processing device performs the following operations. The processing device determines a target set from the candidate sets based on attribute information of a target region of a target subject to be treated. The processing device further designates one or more treatment blocks in the target set as the one or more first treatment blocks.

In some embodiments, the processing device is further configured to perform the following operations. The processing device determines a desired focusing accuracy based on attribute information of a target region of a target subject to be treated. Further, the processing device determines a target ultrasonic frequency of the ultrasonic transducers in the one or more first treatment blocks based on the desired focusing accuracy.

In some embodiments, the processing device is further configured to perform the following operations. The processing device determines possible arrangements of the one or more first treatment blocks in the therapeutic ultrasound probe during a treatment to be performed on a target region of a target subject. For each of the possible arrangements, the processing device determines one or more focusing parameters of the one or more first treatment blocks when the one or more first treatment blocks have the possible arrangement. Further, the processing device determines a target arrangement the one or more first treatment blocks based on the one or more focusing parameters corresponding to the possible arrangement and attribute information of the target region.

In some embodiments, at least one of the treatment blocks includes one or more non-treatment regions that are detachable.

In some embodiments, at least one ultrasonic transducer array of the therapeutic ultrasound probe is movable and/or detachable.

According to an aspect of the present disclosure, a method for treating a target subject using a therapeutic ultrasound system may be provided. The therapeutic ultrasound system may comprise a therapeutic ultrasound probe. The therapeutic ultrasound probe may comprise treatment blocks each of which includes one or more ultrasonic transducer arrays. Each of the one or more ultrasonic transducer arrays may include one or more ultrasonic transducers. The treatment blocks may be movable to rotate around a reference axis and/or adjust an angle with respect to the reference axis. The method may be implemented on a computing device having at least one processor and at least one storage device. The method may include determining, from the treatment blocks, one or more target treatment blocks of the therapeutic ultrasound probe are used for a treatment to be performed on a target region of the target subject. The method may further include causing ultrasonic transducers in the one or more target treatment blocks to emit ultrasonic signals toward the target region.

According to an aspect of the present disclosure, a non-transitory computer readable medium may be provided. The non-transitory computer readable medium comprises at least one set of instructions for treating a target subject using a therapeutic ultrasound system. The therapeutic ultrasound system may comprise a therapeutic ultrasound probe. The therapeutic ultrasound probe may comprise treatment blocks each of which includes one or more ultrasonic transducer arrays. Each of the one or more ultrasonic transducer arrays may include one or more ultrasonic transducers. The treatment blocks may be movable to rotate around a reference axis and/or adjust an angle with respect to the reference axis. When executed by one or more processors of a computing device, the at least one set of instructions causes the computing device to perform a method. The method may include determining, from the treatment blocks, one or more target treatment blocks of the therapeutic ultrasound probe are used for a treatment to be performed on a target region of the target subject. The method may further include causing ultrasonic transducers in the one or more target treatment blocks to emit ultrasonic signals toward the target region.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 5 is a flowchart illustrating an exemplary process for determining one or more first treatment blocks for a treatment of a target region of a target subject according to some embodiments of the present disclosure;

FIG. 6 is a flowchart illustrating an exemplary process for determining one or more first treatment blocks for a treatment of a target region of a target subject according to some embodiments of the present disclosure;

FIG. 7 is a schematic diagram illustrating an exemplary process for determining a target set according to some embodiments of the present disclosure.

DETAILED DESCRIPTION

Figure 1:
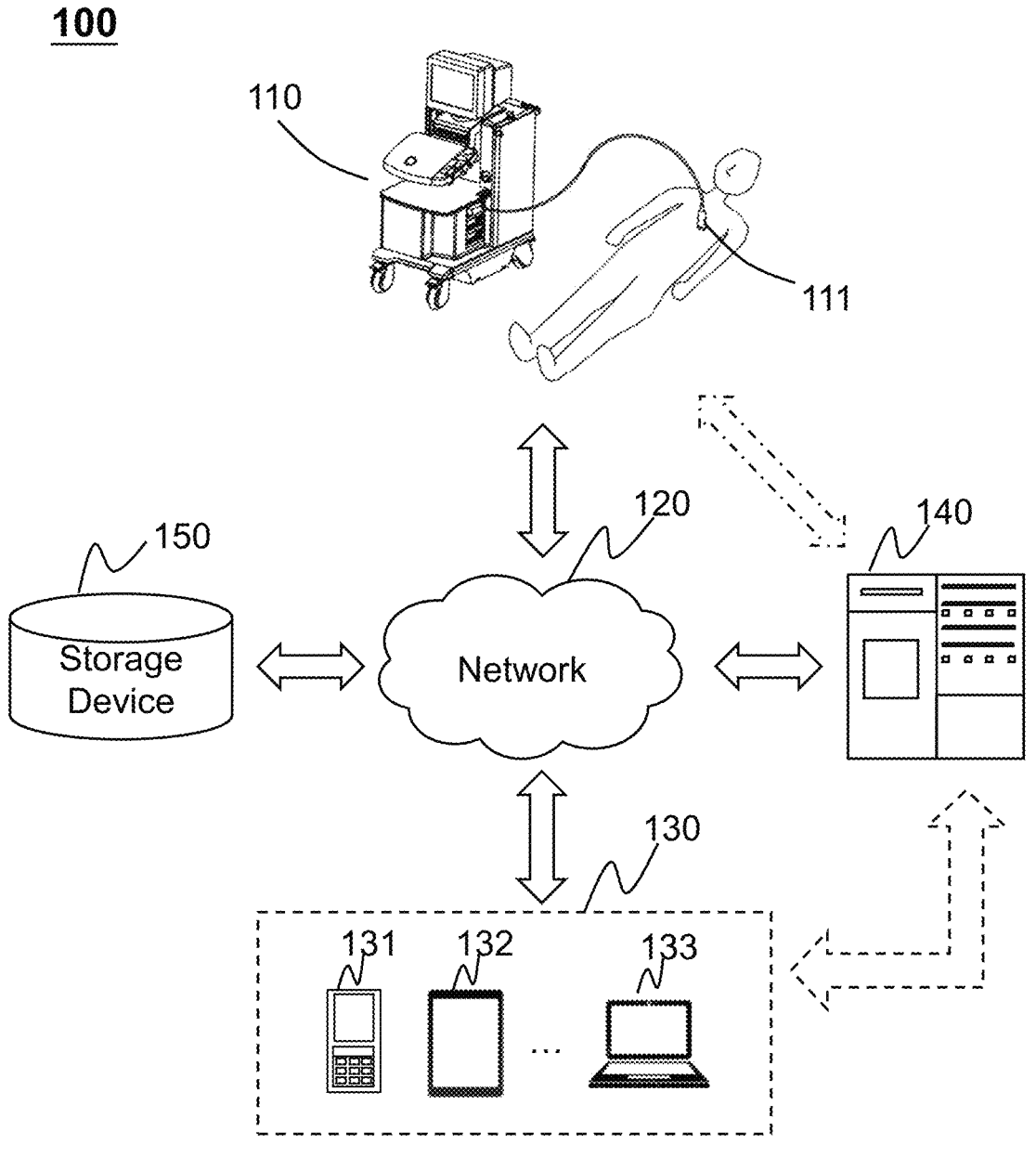
FIG. 1 is a schematic diagram illustrating an exemplary therapeutic ultrasound system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections or assembly of different levels in ascending order. However, the terms may be displaced by another expression if they achieve the same purpose.

It will be understood that when a unit, engine, module, or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

It will be understood that, although the terms "first," "second," "third," "fourth," etc., may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention.

Spatial and functional relationships between elements (for example, between crystal elements) are described using various terms, including "connected," "engaged," "interfaced," and "coupled." Unless explicitly described as being "direct," when a relationship between first and second elements is described in the present disclosure, that relationship includes a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.). As used herein, the term "and/or" includes any and all combinations of one or more of the associated listed items.

An anatomical structure shown in an image of a subject (e.g., a patient) may correspond to an actual anatomical structure existing in or on the subject's body. For example, a body part shown in an image may correspond to an actual body part existing in or on the subject's body, and a feature point in an image may correspond to an actual feature point existing in or on the subject's body. For the convenience of descriptions, an anatomical structure shown in an image and its corresponding actual anatomical structure are used interchangeably. For example, the chest of the subject refers to the actual chest of the subject or a region representing the chest in an image of the subject.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

In the present disclosure, a representation of a subject (e.g., an object, a patient, or a portion thereof) in an image may be referred to as "subject" for brevity. For instance, a representation of an organ, tissue (e.g., a heart, a liver, a lung), or an ROI in an image may be referred to as the organ, tissue, or ROI, for brevity. Further, an image including a representation of a subject, or a portion thereof, may be referred to as an image of the subject, or a portion thereof, or an image including the subject, or a portion thereof, for brevity. Still further, an operation performed on a representation of a subject, or a portion thereof, in an image may be referred to as an operation performed on the subject, or a portion thereof, for brevity. For instance, a segmentation of a portion of an image including a representation of an ROI from the image may be referred to as a segmentation of the ROI for brevity.

A therapeutic ultrasound probe of a therapeutic ultrasound system typically comprises multiple treatment blocks, and each treatment block includes one or more ultrasonic transducer arrays. Each ultrasonic transducer array includes one or more ultrasonic transducers. However, conventional therapeutic ultrasound systems suffer from a limitation: once the treatment blocks are assembled into the therapeutic ultrasound probe, they are fixed and immovable. This lack of adjustability results in a suboptimal fit between the therapeutic ultrasound probe and the target body part to be treated, diminishing treatment accuracy and making it challenging to adapt to varying treatment scenarios. Consequently, there is a need for the development of advanced therapeutic ultrasound systems that offer improved flexibility and precision to meet diverse treatment requirements.

An aspect of the present disclosure relates to a therapeutic ultrasound system. The therapeutic ultrasound system comprises a therapeutic ultrasound probe. The therapeutic ultrasound probe comprises treatment blocks. Each treatment block includes one or more ultrasonic transducer arrays. Each ultrasonic transducer array includes one or more ultrasonic transducers. The treatment blocks of the therapeutic ultrasound probe are movable. For example, the treatment blocks are movable to rotate around a reference axis and/or adjust an angle with respect to the reference axis. Compared with the conventional therapeutic ultrasound systems, the therapeutic ultrasound probe of the present disclosure features movable treatment blocks. This design allows the therapeutic ultrasound probe to conform more precisely to the shape of the target body part, thereby enhancing treatment accuracy and accommodating a variety of treatment scenarios more effectively.

In some embodiments, the therapeutic ultrasound probe is used in combination with a first count of ultrasound channels for a treatment to be performed on a target region of a target subject. In the treatment for the target region, one or more first treatment blocks of the therapeutic ultrasound probe may be used. The one or more first treatment blocks may include all or a portion of the treatment blocks of the therapeutic ultrasound probe. Due to the limited count of the ultrasound channels, a second count needs to be equal to or smaller than the first count, wherein the second count refers to a total count of ultrasound channels that are used to be connected to the one or more first treatment blocks.

To optimize the use of ultrasound channels in a therapeutic ultrasound system, it is desired that the second count is close to the first count. Preferably, the second count is equal to the first count. When the second count is equal to the first count, all ultrasound channels are fully utilized, resulting in improved sound field control, enhanced efficiency of ultrasonic channel usage, and better conservation of system resources.

FIG. 1 is a schematic diagram illustrating an exemplary therapeutic ultrasound system 100 according to some embodiments of the present disclosure. As shown in FIG. 1, the therapeutic ultrasound system 100 may include a therapeutic ultrasound device 110, a network 120, one or more terminals 130, a processing device 140, and a storage device 150. In some embodiments, the therapeutic ultrasound device 110, the terminal(s) 130, the processing device 140, and/or the storage device 150 may be connected to and/or communicate with each other via a wireless connection (e.g., the network 120), a wired connection, or a combination thereof. The connection between the components of the therapeutic ultrasound system 100 may be variable.

The therapeutic ultrasound device 110 may be configured to scan and/or treat a subject (or a part of the subject) using ultrasonic waves. In some embodiments, the subject may include a human being (e.g., a patient), an animal, or a specific portion, organ, and/or tissue thereof. In the present disclosure, the term "object" or "subject" are used interchangeably in the present disclosure. In some embodiments, the therapeutic ultrasound device 110 may include a therapeutic ultrasound probe 111. The therapeutic ultrasound probe 111 may be configured to apply ultrasonic therapy to the subject or obtain medical ultrasound data of the subject. For illustration purposes, the following descriptions are described with reference to a therapeutic ultrasound probe configured for ultrasonic treatment, and not intended to limit the scope of the present disclosure. More descriptions regarding the therapeutic ultrasound probe 111 may be found elsewhere in the present disclosure (e.g., FIGS. 2A-2D and the descriptions thereof).

The network 120 may include any suitable network that can facilitate the exchange of information and/or data for the therapeutic ultrasound system 100. In some embodiments, one or more components of the therapeutic ultrasound system 100 (e.g., the therapeutic ultrasound device 110, the processing device 140, the storage device 150, the terminal(s) 130) may communicate information and/or data with one or more other components of the therapeutic ultrasound system 100 via the network 120. For example, the processing device 140 may obtain data from the therapeutic ultrasound device 110 via the network 120.

The terminal(s) 130 may be connected to and/or communicate with the therapeutic ultrasound device 110, the processing device 140, and/or the storage device 150. For example, the terminal(s) 130 may display a target image of a subject. In some embodiments, the terminal(s) 130 may include a mobile device 131, a tablet computer 132, a laptop computer 133, or the like, or any combination thereof. In some embodiments, the terminal(s) 130 may be part of the processing device 140.

The processing device 140 may process data and/or information obtained from the therapeutic ultrasound device 110, the storage device 150, the terminal(s) 130, or other components of the therapeutic ultrasound system 100. For example, the processing device 140 may determine treatment blocks of the therapeutic ultrasound probe 111 that are used for a treatment to be performed on a target region of a target subject.

In some embodiments, the processing device 140 (e.g., one or more modules illustrated in FIG. 4) may execute instructions and may accordingly be directed to perform one or more processes (e.g., processes 500, 600, and 800) described in the present disclosure. For example, each of the one or more processes may be stored in a storage device (e.g., the storage device 150) as a form of instructions, and invoked and/or executed by the processing device 140. In some embodiments, the processing device 140 is part of the therapeutic ultrasound device 110 or the therapeutic ultrasound probe 111.

In some embodiments, the processing device 140 may be a single server or a server group. In some embodiments, the processing device 140 may be local to or remote from the therapeutic ultrasound system 100. Merely for illustration, only one processing device 140 is described in the therapeutic ultrasound system 100. However, it should be noted that the therapeutic ultrasound system 100 in the present disclosure may also include multiple processing devices. Thus operations and/or method steps that are performed by one processing device 140 as described in the present disclosure may also be jointly or separately performed by the multiple processing devices. For example, if in the present disclosure the processing device 140 of the therapeutic ultrasound system 100 executes both process A and process B, it should be understood that the process A and the process B may also be performed by two or more different processing devices jointly or separately in the therapeutic ultrasound system 100 (e.g., a first processing device executes process A and a second processing device executes process B, or the first and second processing devices jointly execute processes A and B).

The storage device 150 may store data, instructions, and/or any other information. In some embodiments, the storage device 150 may store data obtained from the processing device 140, the terminal(s) 130, and/or the therapeutic ultrasound device 110. For example, the storage device 150 may store data collected by the therapeutic ultrasound device 110. In some embodiments, the storage device 150 may store data and/or instructions that the processing device 140 may execute or use to perform exemplary methods described in the present disclosure.

It should be noted that the above description of the therapeutic ultrasound system 100 is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the therapeutic ultrasound system 100 may include one or more additional components. Additionally or alternatively, one or more components of the therapeutic ultrasound system 100 described above may be omitted. As another example, two or more components of the therapeutic ultrasound system 100 may be integrated into a single component.

Figure 2A:
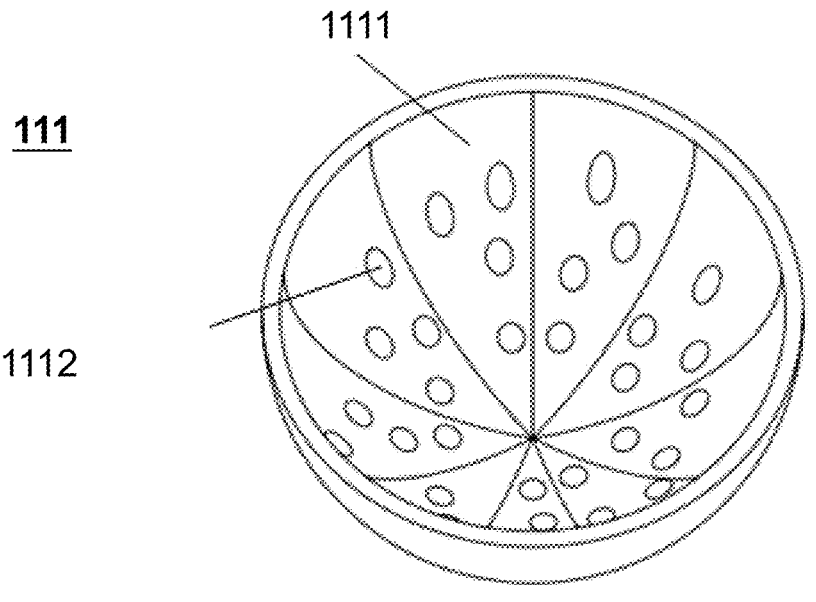
FIGS. 2A and 2B are schematic diagrams illustrating exemplary therapeutic ultrasound probes according to some embodiments of the present disclosure.

FIG. 2A is a schematic diagram illustrating an exemplary therapeutic ultrasound probe 111 according to some embodiments of the present disclosure.

The therapeutic ultrasound probe 111 may be configured to focus ultrasound energy to a target region of a target subject. As uses herein, the target region refers to a region (e.g., a lesion region)) of the target subject that needs to receive an ultrasonic treatment. In some embodiments, the target subject may include a biological or a non-biological object. For example, the target subject may include a patient, an artificial object, etc. As another example, the target subject may include a phantom. The target region may include a specific region, an organ, and/or a tissue of the target subject.

As shown in FIG. 2A, the therapeutic ultrasound probe 111 includes treatment blocks 1111. As used herein, a treatment block 1111 is the smallest assembly unit of the therapeutic ultrasound probe 111 and includes ultrasound transducers for treatment. Each treatment block 1111 includes one or more ultrasonic transducer arrays 1112. Each ultrasonic transducer array 1112 includes one or more ultrasonic transducers. An ultrasonic transducer refers to a device that converts acoustic energy and electrical energy into each other within an ultrasonic frequency range. The ultrasonic transducer may include a transmitting transducer, a receiving transducer, or a dual-function transducer. The transmitting transducer may be configured to convert electrical energy into an ultrasonic signal and emit the ultrasonic signal. The receiving transducer may be configured to receive ultrasonic signals and convert them into electrical energy. The dual-function transducer may be configured to emit ultrasonic waves and receive the reflected ultrasonic signals.

In some embodiments, the ultrasonic transducer array(s) 1112 may be arranged on an inner surface of the therapeutic ultrasound probe 111. The inner surface of the therapeutic ultrasound probe 111 refers to a surface of the therapeutic ultrasound probe 111 that is in contact with the target region in treatment directly or indirectly (e.g., via coupling agent). In some embodiments, the one or more ultrasonic transducer arrays 1112 are randomly distributed on the corresponding treatment block 1111, which may obtain a relatively small sound field grating lobe. Alternatively, the one or more ultrasonic transducer arrays 1112 are distributed on the corresponding treatment block 1111 according to a certain rule. For example, the one or more ultrasonic transducer arrays 1112 include a plurality of ultrasonic transducer arrays 1112, and each adjacent ultrasonic transducer arrays 1112 in the plurality of ultrasonic transducer arrays 1112 are distributed on the corresponding treatment block 1111 at a preset distance.

In some embodiments, the one or more ultrasonic transducers are randomly distributed in the corresponding ultrasonic transducer array 1112. Alternatively, the one or more ultrasonic transducers may be distributed in the corresponding ultrasonic transducer array 1112 according to a certain rule, for example, arranged linearly or in a matrix. In some embodiments, different treatment blocks 1111 include the same count or different counts of ultrasonic transducer arrays 1112. In some embodiments, different ultrasonic transducer arrays 1112 include the same count or different counts of ultrasonic transducers.

For example, as shown in FIG. 2A, the inner surface of the therapeutic ultrasound probe 111 is a hemispherical surface with a diameter of 35 cm. The therapeutic ultrasound probe 111 includes 9 treatment blocks 1111 with the same size. 4 ultrasonic transducer arrays 1112 are randomly distributed on each treatment block 1111. 32 ultrasonic transducers are randomly distributed in each ultrasonic transducer array 1112.

Figure 2B:
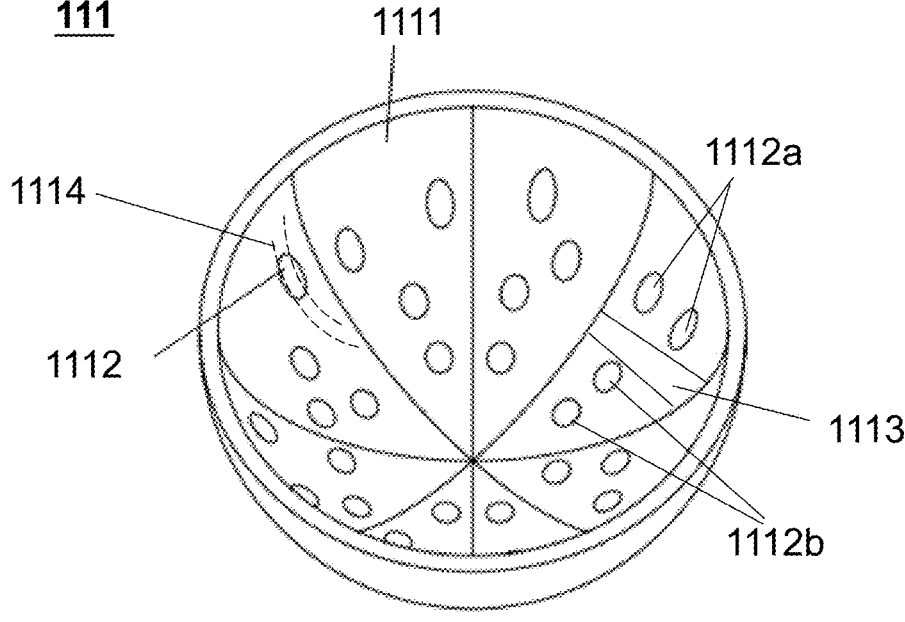

As another example, as shown in FIG. 2B, the inner surface of the therapeutic ultrasound probe 111 is a hemispherical surface with a diameter of 32 cm. The therapeutic ultrasound probe 111 includes 8 treatment blocks 1111 with the same size. 4 ultrasonic transducer arrays 1112 are randomly distributed on each treatment block 1111. 16 ultrasonic transducers are randomly distributed in each ultrasonic transducer array 1112.

In some embodiments, the treatment blocks 10 are connected to each other through vertex connection, boundary connection, or some mounting components (mounting brackets). In some embodiments, sizes of the treatment blocks 1111 may be the same or different. In some embodiments, a treatment block 1111 may include a rigid substrate, such as a metal or polymer substrate. Alternatively, a treatment block 1111 may include a flexible substrate. In some embodiments, the therapeutic ultrasound probe 111 may include one or more non-treatment blocks. As used herein, a non-treatment block of the therapeutic ultrasound probe 111 refers to a block of the therapeutic ultrasound probe 111 that does not include any ultrasound transducer arrays. The one or more non-treatment blocks are designed to use in conjunction with the treatment blocks 1111 for assembling the therapeutic ultrasound probe 111. In some embodiments, the one or more non-treatment blocks are detachable from the therapeutic ultrasound probe 111.

In some embodiments, ultrasonic frequencies of different ultrasonic transducers may be the same or different. In some embodiments, the ultrasonic frequencies of the ultrasonic transducers may be adjustable. In some embodiments, when one or more first treatment blocks of the therapeutic ultrasound probe 111 are used for a treatment to be performed on the target region and the ultrasonic frequencies of the ultrasonic transducers in the one or more first treatment blocks are different or adjustable, the processing device 140 may determine a desired focusing accuracy based on attribute information of the target region, and further determine a target ultrasonic frequency of the ultrasonic transducers in the one or more first treatment blocks based on the desired focusing accuracy. More descriptions regarding the determination of the target ultrasonic frequency may be found elsewhere in the present disclosure (e.g., FIG. 8 and the descriptions thereof).

In some embodiments, when the treatment blocks 1111 are assembled into the therapeutic ultrasound probe 111, the inner surface of the therapeutic ultrasound probe 111 is an axisymmetric surface or a portion of the axisymmetric surface, and the reference axis may be a symmetry axis of the axisymmetric surface. For example, the inner surface of the therapeutic ultrasound probe 111 is a surface formed by rotating an axisymmetric curve (e.g., a parabola) by 180° around its axis of symmetry. Merly by way of example, as shown in FIG. 2A, the inner surface of the therapeutic ultrasound probe 111 is a hemispherical concave surface.

In some embodiments, the inner surface may be a concave surface. In some embodiments, when the treatment blocks 1111 are assembled into the therapeutic ultrasound probe 111, the inner surface of the therapeutic ultrasound probe 111 may conform to the shape of a target body part. The target body part refers to a body part that the therapeutic ultrasound probe 111 can treat. Different therapeutic ultrasound probes 111 may be designed for treating different target body parts with different shapes. Exemplary target body parts may include the head, the neck, the body, a shoulder, an arm, the chest, the heart, the stomach, a blood vessel, a knee, a foot, etc., or any combination thereof.

Specifically, when the treatment blocks 1111 are assembled into the therapeutic ultrasound probe 111, the inner surface of the therapeutic ultrasound probe 111 may conform to the shape of the target body part. For example, the target body part is the head, and the inner surface of the therapeutic ultrasound probe 111 is a portion of a spherical surface.

In some embodiments, the treatment blocks 1111 are movable. For example, the movement of the treatment blocks is supported by various components such as a bearing (e.g., a rolling bearing, a sliding bearing, etc.), a hinge, a rotary joint, a pivot point, etc. In some embodiments, the treatment blocks may be moved manually by a user. Alternatively, the treatment blocks may be moved automatically by, such as a drive device (e.g., a motor, a movement transmission device).

Figure 2C:
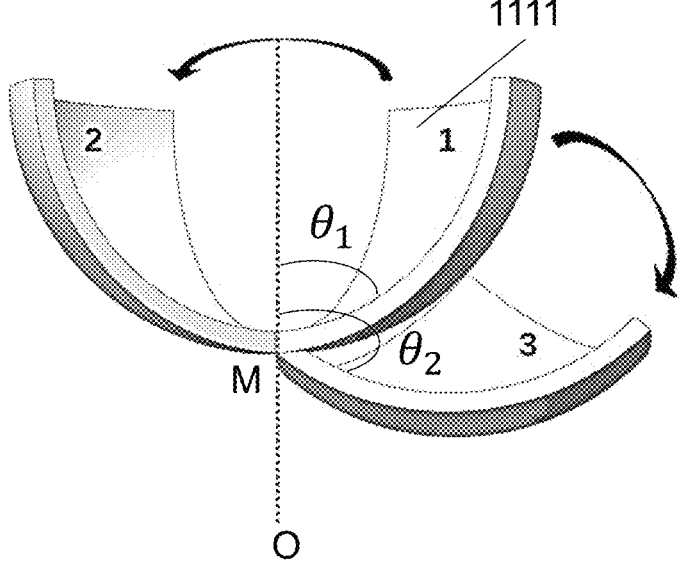
FIG. 2C is a side view of exemplary movements of a treatment block of a therapeutic ultrasound probe according to some embodiments of the present disclosure.
Figure 2D:
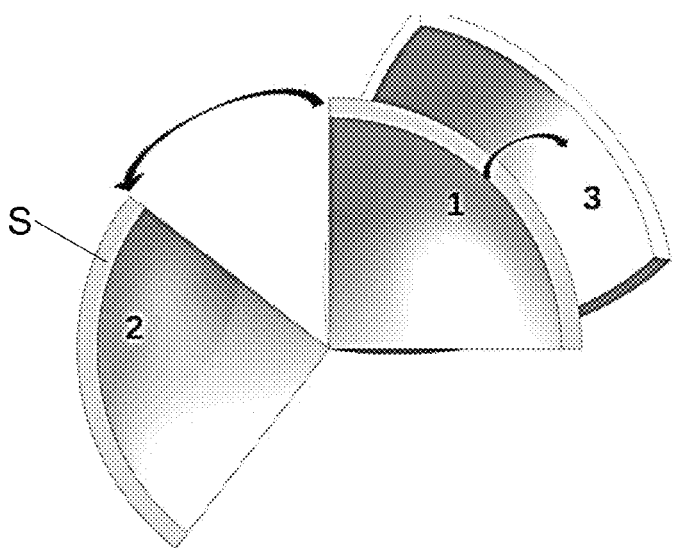
FIG. 2D is a top view of exemplary movements of a treatment block of a therapeutic ultrasound probe according to some embodiments of the present disclosure.

In some embodiments, the treatment blocks 1111 may be movable to rotate around a reference axis and/or adjust an angle with respect to the reference axis. For example, FIG. 2C is a side view of exemplary movements of a treatment block 1111 of the therapeutic ultrasound probe 111 according to some embodiments of the present disclosure. FIG. 2D is a top view of exemplary movements of the treatment block 1111 of the therapeutic ultrasound probe 111 according to some embodiments of the present disclosure. As shown in FIG. 20, when the treatment blocks 1111 are assembled into the therapeutic ultrasound probe 111, the therapeutic ultrasound probe 111 has a hollow hemispherical shape with a symmetry axis O that passes through the vertex M. The reference axis is the symmetry axis O. The treatment block 1111 may move from a position 1 to a position 2 by rotating around the reference axis O along a circumference of the inner surface. The treatment block 1111 may move from the position 1 to a position 3 by adjusting the angle with respect to the reference axis O from $\theta_1$ to $\theta_2$.

The therapeutic ultrasound probe 111 with movable treatment blocks 1111 can be used to treat different users precisely and meet diverse treatment requirements. For example, since sizes of the heads of different patients are different, when the treatment blocks 1111 are assembled into the therapeutic ultrasound probe 111 to treat a specific patient, the treatment blocks 1111 may rotate around the reference axis and/or adjust the angle with respect to reference axis, so that the inner surface of the therapeutic ultrasound probe 111 may conform to the shape of the head of the specific patient.

In some embodiments, at least one of the treatment blocks 1111 is detachable from the therapeutic ultrasound probe 111. That is, at least one of the treatment blocks 1111 can be removed from the therapeutic ultrasound probe 111. In some embodiments, then the therapeutic ultrasound probe 111 is used to a treatment of the target region of the target subject, a portion of the treatment blocks 1111 (e.g., the one or more first treatment blocks 1111) may be assembled into the therapeutic ultrasound probe 111, and the remaining treatment blocks 1111 may be removed from the therapeutic ultrasound probe 111. The portion of treatment blocks 1111 may be assembled into the therapeutic ultrasound probe 111 in various ways. For example, the portion of the treatment blocks 1111 are connected to each other by a vertex connection, a boundary connection, or by some mounting components (e.g., a mounting bracket). The detachable design of the treatment blocks 1111 allows for greater flexibility in assembling the therapeutic ultrasound probe 111. Only the treatment blocks required for a specific application need to be installed, while the remaining treatment blocks can be removed. This modular approach enables more adaptable configurations, ensuring that the therapeutic ultrasound probe 111 can be tailored to meet various treatment scenarios without the constraints imposed by unused treatment blocks.

In some embodiments, each treatment block 111 can be controlled individually for treatment purposes. All treatment blocks 111 are assembled into the therapeutic ultrasound probe 111, and when the treatment is performed, a portion of the treatment blocks 1111 (e.g., the one or more first treatment blocks 1111) are activated for treatment while the remaining treatment blocks 1111 are not activated.

In some embodiments, the therapeutic ultrasound probe 111 is used in combination with a first count of ultrasound channels for a treatment to be performed on the target region of the target subject. An ultrasonic channel is configured to transmit an instruction or a signal to an ultrasonic transducer to control the ultrasonic transducer to emit ultrasonic waves. Each ultrasonic channel may be connected to one or more ultrasonic transducers and capable of controlling the connected ultrasonic transducer(s).

In the treatment for the target region, one or more first treatment blocks of the therapeutic ultrasound probe 111 may be used. The one or more first treatment blocks may include all or a portion of the treatment blocks of the therapeutic ultrasound probe 111. Due to the limited count of the ultrasound channels, a second count needs to be equal to or smaller than the first count, wherein the second count refers to a total count of ultrasound channels that are used to be connected to the one or more first treatment blocks.

To optimize the use of ultrasound channels in a therapeutic ultrasound system, it is desired that the second count is close to the first count. Preferably, the second count is equal to the first count. For example, the first count is 256. If a count of ultrasound channels that are used to be connected to each first treatment block is 64 and a count of the one or more first treatment blocks is 4, the second count is 256. That is, the first count is equal to the second count. When the second count is equal to the first count, all ultrasound channels are fully utilized, resulting in improved sound field control, enhanced efficiency of ultrasonic channel usage, and better conservation of system resources.

In some embodiments, the one or more first treatment blocks include a portion of the treatment blocks of the therapeutic ultrasound probe 111, one or more second treatment blocks other than the one or more first treatment blocks are removed from the therapeutic ultrasound probe 111 for the treatment of the target subject. Alternatively, the one or more second treatment blocks are remained in the therapeutic ultrasound probe 111 but not activated in the treatment of the target subject.

In some embodiments, as illustrated in FIG. 1, the therapeutic ultrasound system 100 may include the processing device 140. The processing device 140 may be configured to, for each of the treatment blocks, determine a third count of ultrasound channels that are used to connected to the treatment block, and select the one or more first treatment blocks from the treatment blocks based on the first count and the third count corresponding to each of the treatment blocks. More descriptions regarding the determination of the one or more first treatment blocks may be found elsewhere in the present disclosure (e.g., FIG. 5 and the descriptions thereof).

In some embodiments, at least one of the treatment blocks 1111 includes one or more non-treatment regions that are detachable. As used herein, a non-treatment region of a treatment block refers to a region of the treatment block that is not used for treatment. For example, the non-treatment region does not include any ultrasonic transducer array. As another example, the non-treatment region includes ultrasonic transducer array(s), but these ultrasonic transducer array(s) are used for monitoring the treatment process instead of treating the target region.

Merely by way of example, as shown in FIG. 2B, a region 1113 is a non-treatment region of a treatment block 1111. If the target body part of the target subject is relatively small, a distance between the ultrasonic transducer arrays 1112a and 1112b located on both sides of the region 1113 needs to be reduced to improve focus accuracy. In this case, the non-treatment region 1113 needs to be removed from the therapeutic ultrasound probe 111. The usage flexibility and the focusing accuracy of the therapeutic ultrasound probe 111 may be improved by arranging the one or more non-treatment regions that are detachable on the treatment blocks.

In some embodiments, at least one ultrasonic transducer array 1112 of the therapeutic ultrasound probe 111 may be movable and/or detachable. For example, the movement of an ultrasonic transducer array 1112 is supported by various components such as a bearing (e.g., a rolling bearing, a sliding bearing, etc.), a hinge, a rotary joint, a pivot point, etc. In some embodiments, the ultrasonic transducer array 1112 is moved manually by a user. Alternatively, the ultrasonic transducer array 1112 is moved automatically by, such as a drive device (e.g., a motor, a movement transmission device). Merely by way of example, as shown in FIG. 2B, an ultrasonic transducer array 1112 is moved via a sliding bearing 1114. In some embodiments, the at least one ultrasonic transducer array 1112 may be moved manually by a user. Alternatively, the at least one ultrasonic transducer array 1112 may be moved automatically by, such as a drive device. The usage flexibility and the focusing accuracy of the therapeutic ultrasound probe 111 may be improved by arranging the at least one ultrasonic transducer array 1112 that is movable and/or detachable.

As described elsewhere in the present disclosure, the conventional therapeutic ultrasound systems suffer from a limitation: once the treatment blocks are assembled into the therapeutic ultrasound probe, they are fixed and immovable. This lack of adjustability results in a suboptimal fit between the therapeutic ultrasound probe and the target body part to be treated, diminishing treatment accuracy and making it challenging to adapt to varying treatment scenarios.

According to the therapeutic ultrasound system of the present disclosure, the treatment blocks are movable. For example, the treatment blocks may be movable to rotate around a reference axis and/or adjust an angle with respect to the reference axis. Compared with the conventional therapeutic ultrasound systems, the therapeutic ultrasound probe of the present disclosure features movable treatment blocks. This design allows the therapeutic ultrasound probe to conform more precisely to the shape of the target body part, thereby enhancing treatment accuracy and accommodating a variety of treatment scenarios more effectively.

Figure 3:
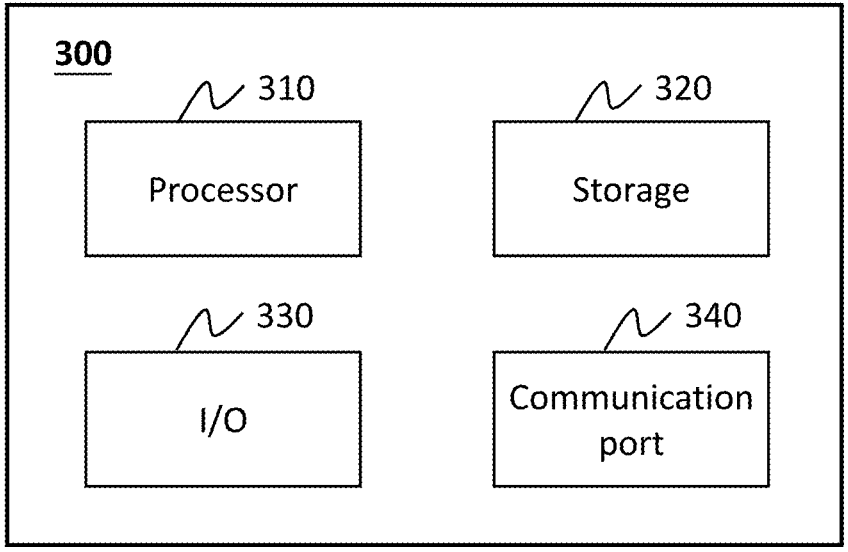
FIG. 3 is a schematic diagram illustrating exemplary hardware and/or software components of a computing device according to some embodiments of the present disclosure.

FIG. 3 is a schematic diagram illustrating exemplary hardware and/or software components of a computing device according to some embodiments of the present disclosure. In some embodiments, the processing device 140 may be implemented on the computing device 300. As illustrated in FIG. 3, the computing device 300 may include a processor 310, a storage 320, an input/output (I/O) 330, and a communication port 340.

The processor 310 may execute computer instructions (program code) and perform functions of the processing device 140 in accordance with techniques described herein. The computer instructions may include routines, programs, objects, components, signals, data structures, procedures, modules, and functions, which perform particular functions described herein. Merely for illustration purposes, only one processor is described in the computing device 300. However, it should be noted that the computing device 300 in the present disclosure may also include multiple processors, and thus operations of a method that are performed by one processor as described in the present disclosure may also be jointly or separately performed by the multiple processors.

The storage 320 may store data/information obtained from the therapeutic ultrasound device 110, the terminal device 130, the storage device 150, or any other component of the therapeutic ultrasound system 100. In some embodiments, the storage 320 may include a mass storage device, a removable storage device, a volatile read-and-write memory, a read-only memory (ROM), or the like, or any combination thereof. In some embodiments, the storage 320 may store one or more programs and/or instructions to perform exemplary methods described in the present disclosure.

The I/O 330 may input or output signals, data, or information. In some embodiments, the I/O 330 may enable user interaction with the processing device 140. In some embodiments, the I/O 330 may include an input device and an output device.

The communication port 340 may be connected to a network (e.g., the network 120) to facilitate data communications. The communication port 340 may establish connections between the processing device 140 and the therapeutic ultrasound device 110, the terminal device 130, or the storage device 150. The connection may be a wired connection, a wireless connection, or combination of both that enables data transmission and reception.

It should be noted that the above description of the computing device 300 is merely provided for the purposes of illustration, and not intended to limit the scope of the present disclosure. For persons having ordinary skills in the art, multiple variations and modifications may be made under the teachings of the present disclosure.

Figure 4:
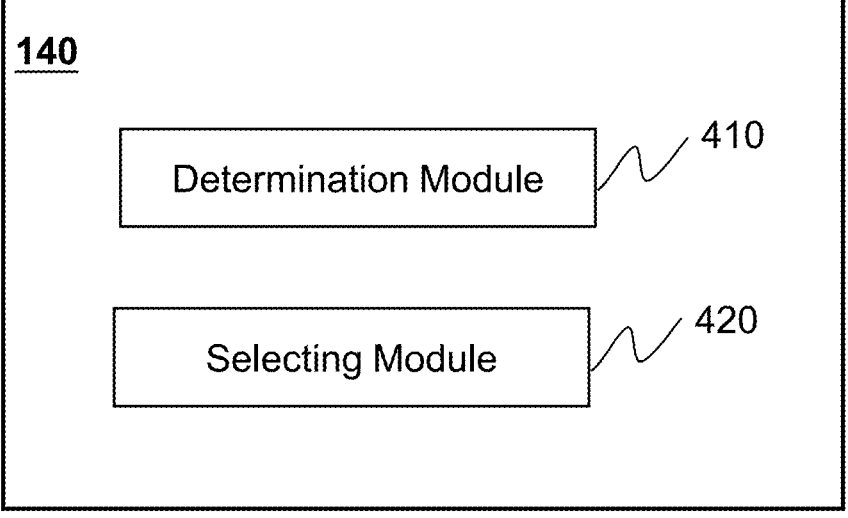
FIG. 4 is a block diagram illustrating an exemplary processing device according to some embodiments of the present disclosure.

FIG. 4 is a block diagram illustrating exemplary processing device 140 according to some embodiments of the present disclosure.

As shown in FIG. 4, the processing device 140 may include a determination module 410 and a selecting module 420. As described in FIG. 1, the therapeutic ultrasound system 100 in the present disclosure may also include multiple processing devices, and the determination module 410 and the selecting module 420 may be components of different processing devices.

In some embodiments, the determination module 410 is configured to, for each of treatment blocks, determine a third count of ultrasound channels that are used to be connected to the treatment block. When the third counts corresponding to the treatment blocks are the same, the determination module 410 is configured to determine a fourth count of the one or more first treatment blocks based on the first count and the third count, and the selecting module 420 is configured to select a portion of the treatment blocks as the one or more first treatment blocks, the count of the selected portion of the treatment blocks being equal to the fourth count. When the third counts corresponding to at least two of the treatment blocks are different, the determination module 410 is configured to determine one or more candidate sets of treatment blocks based on the third count corresponding to each treatment block, and the selecting module 420 is configured to select the one or more first treatment blocks based on the one or more candidate sets.

More descriptions regarding the determining the one or more first treatment blocks may be found elsewhere in the present disclosure. See, e.g., operations 520-550 in FIG. 5, and relevant descriptions thereof.

In some embodiments, the determination module 410 is configured to determine a desired focusing accuracy based on attribute information of the target region of the target subject to be treated, and further determine a target ultrasonic frequency of the ultrasonic transducers in the one or more first treatment blocks based on the desired focusing accuracy. More descriptions regarding the determination of the desired focusing accuracy and the target ultrasonic frequency may be found elsewhere in the present disclosure. See, e.g., operations 810 and 820 in FIG. 8, and relevant descriptions thereof.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, any one of the modules may be divided into two or more units. For instance, the processing device 140 may include one or more additional modules, such as a storage module (not shown) for storing data.

FIG. 5 is a flowchart illustrating an exemplary process 500 for determining one or more first treatment blocks for a treatment of a target region of a target subject according to some embodiments of the present disclosure.

The one or more first treatment blocks may be one or more treatment blocks of the therapeutic ultrasound probe 111 that are used to emit ultrasonic waves to the target region. As described elsewhere in the present disclosure, the therapeutic ultrasound probe 111 may comprise treatment blocks. Each treatment block may include one or more ultrasonic transducer arrays. Each ultrasonic transducer array includes one or more ultrasonic transducers.

In 510, for each of the treatment blocks, the processing device 140 (e.g., the determination module 410) may determine a third count of ultrasound channels that are used to be connected to the treatment block.

During the treatment, one or more ultrasonic transducers of the treatment block may be connected to one ultrasound channel and controlled by the connected ultrasound channel, for example, four ultrasonic transducers of the treatment block may share one ultrasound channel. The third count of ultrasound channels refers to the total count of ultrasound channels that are connected to the ultrasonic transducer(s) of the treatment block when the treatment block is enabled. For example, the processing device 140 may determine the third count of ultrasound channels that are used to be connected to the treatment block according to Equation (1) as below:

$$M = \sum_{i=1}^{i=n} \frac{U_i}{Q_i}, \tag{1}$$

where, i denotes a serial number of the one or more ultrasonic transducer arrays of the treatment block, n denotes a total number of the one or more ultrasonic transducer arrays of the treatment block, $U_i$ denotes a number of ultrasonic transducers contained in the $i^{th}$ ultrasonic transducer array, and $Q_i$ denotes a number of ultrasonic transducers in the $i^{th}$ ultrasonic transducer array connected to one ultrasound channel. If M is an integer, the third count is equal to the M; if M is not an integer, the third count is equal to the greatest integer smaller than M. $Q_i$ may be the same or different for different ultrasonic transducer arrays.

As described in FIG. 2A, the therapeutic ultrasound probe 111 is used in combination with the first count of ultrasound channels. Further, the processing device 140 may select the one or more first treatment blocks from the treatment blocks based on the first count and the third count corresponding to each of the treatment blocks. In some embodiments, when the third counts corresponding to the treatment blocks are the same, the processing device 140 may perform operations 520 and 530. In some embodiments, when the third counts corresponding to at least two of the treatment blocks are different, the processing device 140 may perform operations 540 and 550.

In 520, when the third counts corresponding to the treatment blocks are the same, the processing device 140 (e.g., the determination module 410) may determine a fourth count of the one or more first treatment blocks based on the first count and the third count.

In some embodiments, the fourth count is determined based on a ratio of the first count to the third count. As described in FIG. 2A, the second count is equal to or smaller than the first count. The second count is equal to the product of the fourth count and the third count, and therefore, the fourth count is smaller than or equal to the ratio of the first count to the third count.

In some embodiments, the fourth count is the greatest integer equal to or smaller than the ratio of the first count to the third count.

For example, the therapeutic ultrasound probe 111 includes 8 treatment blocks. Each treatment block includes 4 ultrasonic transducer arrays. Each ultrasonic transducer array includes 16 ultrasonic transducers. Each ultrasound channel is connected to one ultrasonic transducer. Therefore, the third count is 64 (i.e., 16*4/1). If the first count is 256, the fourth count may be equal to 4 (i.e., 256/64).

As another example, the therapeutic ultrasound probe 111 includes 9 treatment blocks. Each treatment block includes 4 ultrasonic transducer arrays. Each ultrasonic transducer array includes 32 ultrasonic transducers. Each ultrasound channel is connected to 4 ultrasonic transducers. Therefore, the third count is 32 (i.e., 32*4/4). If the first count is 128, the fourth count may be equal to 4 (i.e., 128/32).

In 530, the processing device 140 (e.g., the selecting module 420) may select a portion of the treatment blocks as the one or more first treatment blocks, the count of the selected portion of the treatment blocks being equal to the fourth count.

In some embodiments, the ultrasonic transducers of different treatment blocks have the same arrangement, and the one or more first treatment blocks may be selected randomly from the treatment blocks. As used herein, an arrangement of the ultrasonic transducers of a treatment block refers to a distribution of the ultrasonic transducers on the treatment block. The arrangement of the ultrasonic transducers in a treatment block may affect the ultrasonic emission mode of the treatment block. If different treatment blocks have the same arrangement of ultrasonic transducers, the first treatment block(s) can be selected randomly from the treatment blocks.

In some embodiments, the one or more first treatment blocks may be selected from the treatment blocks further based on attribute information of the target region of the target subject to be treated. Exemplary attribute information of the target region may include a location, a size, a shape, etc. of the target region, information relating to a lesion in the target region, or the like, or any combination thereof. For example, the processing device 140 may select the treatment blocks close to the target region or the lesion in the target region of the target subject as the one or more first treatment blocks. As another example, the processing device 140 may select the treatment blocks covering the target region as the one or more first treatment blocks.

In some embodiments, the attribute information of the target region may be stored in a storage device (e.g., the storage device 150), and the processing device 140 may retrieve the attribute information of the target region from the storage device. In some embodiments, the processing device 140 may obtain a medical image of the target subject, and determine the attribute information of the target region based on the medical image and the fourth count. The medical image may include a 2D image (e.g., a slice image), a 3D image, a 4D image (e.g., a series of 3D images over time), and/or any related image data (e.g., scan data, projection data), or the like. In some embodiments, the medical image may be generated by a biomedical imaging technique. For example, the medical image may include a DR image, an MR image, a PET image, a CT image, a PET-CT image, a PET-MR image, an ultrasound image, etc.

For example, the target region may be segmented from the medical image manually by a user (e.g., a doctor, an imaging specialist, a technician) by, for example, drawing a bounding box on the medical image displayed on a user interface. Alternatively, the medical image may be segmented by the processing device 140 automatically according to an image segmentation algorithm. Exemplary image segmentation algorithms may include a thresholding segmentation algorithm, a compression-based algorithm, an edge detection algorithm, a machine learning-based segmentation algorithm, or the like, or any combination thereof. Further, the processing device 140 may determine the attribute information of the target region (e.g., the location, the size, the shape, etc. of the target region) according to the segmentation result.

As another example, the processing device 140 may input the medical image and an image of the therapeutic ultrasound probe into a trained model (e.g., a machine learning model), and the model may output a selection result of the one or more first treatment blocks.

In some embodiments, the ultrasonic transducers of different treatment blocks have different arrangements, the processing device 140 may select the first treatment block(s) by considering arrangement information of the ultrasonic transducers in each treatment block, the attribute information of the target region, etc., to achieve a better focusing accuracy and treatment effect. For example, the processing device 140 may determine candidate sets (also referred to as first candidate sets) of treatment blocks, the count of treatment blocks in each candidate set being equal to the fourth count. For each of the candidate sets, the processing device 140 may determine one or more focusing parameters of the candidate set based on arrangement information of the ultrasonic transducers in each treatment block in the candidate set. Further, the processing device 140 may determine a target set from the candidate sets based on the one or more focusing parameters of each candidate set and the attribute information of the target region, and designate the treatment blocks in the target set as the one or more first treatment blocks. More descriptions regarding the determination of the one or more first treatment blocks when the ultrasonic transducers of different treatment blocks have different arrangements may be found elsewhere in the present disclosure (e.g., FIG. 6 and the descriptions thereof).

In 540, when the third counts corresponding to at least two of the treatment blocks are different, the processing device 140 (e.g., the determination module 410) may determine one or more second candidate sets of treatment blocks based on the third count corresponding to each treatment block.

As described in FIG. 2A, the second count is equal to or smaller than the first count, therefore, a sum of the third counts corresponding to the treatment blocks in each second candidate set is smaller than or equal to the first count.

In some embodiments, a difference between the sum and the first count is not greater than a threshold value. The threshold value may be set manually by a user (e.g., an engineer) according to an experience value or a default setting of the therapeutic ultrasound system 100, or determined by the processing device 140 according to an actual need. The smaller the difference between the first count and the sum, the more the ultrasound channels are used, thereby achieving the higher utilization efficiency of the ultrasonic channels. For example, the processing device 140 may determine initial sets of treatment blocks. The sum of the third counts corresponding to the treatment blocks in each initial set is smaller than or equal to the first count. Further, for each initial set, the processing device 140 may determine the difference between the sum of the third counts corresponding to the initial set and the first count. Then, the processing device may determine one or more initial sets having the differences not greater than the threshold value as the one or more second candidate sets.

In 550, the processing device 140 (e.g., the selecting module 420) may select the one or more first treatment blocks based on the one or more second candidate sets.

In some embodiments, the processing device 140 selects the one or more treatment blocks in any one second candidate set as the one or more first treatment blocks.

In some embodiments, the processing device 140 selects the one or more treatment blocks in the second candidate set that corresponds to the smallest difference as the one or more first treatment blocks. The second candidate set corresponding to the smallest difference can utilize the maximum number of ultrasound channels.

In some embodiments, the one or more second candidate sets include multiple second candidate sets, the processing device 140 determines a target set from the second candidate sets based on the attribute information of the target region of the target subject to be treated, and designates one or more treatment blocks in the target set as the one or more first treatment blocks. For example, if the size of the target region is relatively large or the shape of the target region is relatively irregular, the processing device 140 determines a second candidate set with more treatment blocks from the second candidate sets as the target set. In this way, there are more degrees of freedom to adjust the one or more first treatment blocks to conform to and fit the target region, which can achieve better focusing effect.

In some embodiments, as described FIGS. 2A and 2B, at least one of the treatment blocks 1111 includes one or more non-treatment regions that are detachable. When the one or more first treatment blocks include one or more non-treatment regions, the processing device 140 may determine whether at least part of one or more non-treatment regions of the one or more first treatment blocks needs to be removed based on the attribute information of the target region of the target subject. For example, if the head of the target subject is relatively small, at least part of non-treatment regions of the one or more first treatment blocks are removed to achieve higher focusing accuracy. As another example, to select the target set, for each first candidate set, focusing accuracies corresponding to the multiple sets of focusing parameters may be determined (which will be described in detail in connection with FIG. 6). If the focusing accuracy corresponding to each set of focusing parameters does not satisfy requirements (e.g., is smaller a focusing accuracy threshold), the at least part of non-treatment regions of the one or more first treatment blocks may be removed, and then the one or more first treatment blocks may be reassembled after removing the at least part of non-treatment regions.

In the conventional therapeutic ultrasound systems, the ultrasonic signals often deviate from the central axis of the therapeutic ultrasound probe when acting on the target region. Usually, the ultrasonic transducers farther away from the target region contribute less energy to the focus of the ultrasonic signals (also referred to as ultrasonic waves) on the target region, but they occupy the ultrasonic channels of the therapeutic ultrasound system, which reduces the utilization efficiency of the ultrasonic channels and the focusing accuracy of the ultrasonic signals. If the ultrasonic channels are increased, the complexity of the therapeutic ultrasound system also increases greatly. According to some embodiments, the one or more first treatment blocks are determined based on the attribute information of the target region of the target subject to achieve improved utilization efficiency of the ultrasonic channels and focusing accuracy of the ultrasonic signals, thereby improving the effect of the treatment of the target region.

FIG. 6 is a flowchart illustrating an exemplary process 600 for determining one or more first treatment blocks for a treatment of a target region of a target subject according to some embodiments of the present disclosure. In some embodiments, one or more operations of the process 600 may be performed to achieve at least part of operation 530 as described in connection with FIG. 5.

The one or more first treatment blocks may be one or more treatment blocks of the therapeutic ultrasound probe 111. As described elsewhere in the present disclosure, the therapeutic ultrasound probe 111 may comprise treatment blocks. Each treatment block may include one or more ultrasonic transducer arrays. Each ultrasonic transducer array includes one or more ultrasonic transducers. The third counts corresponding to the treatment blocks are the same, and the ultrasonic transducers of different treatment blocks have different arrangements.

In 610, the processing device 140 (e.g., the selecting module 420) may determine candidate sets of treatment blocks, the count of treatment blocks in each candidate set being equal to the fourth count.

In some embodiments, the processing device 140 may randomly select a portion of the treatment blocks as a candidate set of treatment blocks, wherein the count of treatment blocks in the selected portion is equal to the fourth count.

In 620, for each of the candidate sets, the processing device 140 (e.g., the selecting module 420) may determine one or more focusing parameters of the candidate set based on arrangement information of the ultrasonic transducers in each treatment block in the candidate set.

Exemplary arrangement information of the ultrasonic transducers in a treatment block includes a position, a diameter, an angle, etc., of each ultrasonic transducer in the treatment block, a distribution of the ultrasonic transducers (e.g., a density of the ultrasonic transducers, a distance between different ultrasonic transducers), or the like, or any combination thereof. Exemplary focusing parameters include a focusing position, a focusing size, a focusing intensity, or the like, or any combination thereof. For example, the focusing position is determined according to the positions of the ultrasonic transducers in each treatment block and a position of each treatment block after the treatment blocks are assembled into the therapeutic ultrasound probe. As another example, the focusing intensity is determined according to the diameter of each ultrasonic transducer and an ultrasonic wave length or ultrasonic frequency of the ultrasonic signals emitted or received by each ultrasonic transducer.

In some embodiments, the processing device 140 determines the one or more focusing parameters using a focusing parameter determination model based on the arrangement information. Specifically, the arrangement information is input into the focusing parameter determination model, and the focusing parameter determination model outputs the one or more focusing parameters. The focusing parameter determination model may be a trained model for determining or estimating focusing parameters. In some embodiments, the focusing parameter determination model may include a machine learning model (e.g., a deep learning model). Exemplary deep learning models may include a deep neural network (DNN) model, a convolutional Neural Network (CNN) model, a recurrent neural network (RNN) model, a feature pyramid network (FPN) model, a generative adversarial network (GAN) model, or the like, or any combination thereof.

In some embodiments, since the treatment blocks are movable, they can be arranged in different positions and/or angles when assembled into the therapeutic ultrasound probe. The arrangement of the treatment blocks also affects the focusing parameters and needs to be considered. For example, for each candidate set, the one or more focusing parameters of the candidate set include multiple sets of focusing parameters corresponding to different possible arrangements of the treatment blocks in the candidate set. A set of focusing parameters corresponding to a possible arrangement of the treatment blocks in the candidate set is determined by inputting the arrangement information and second arrangement information corresponding to the possible arrangement of the treatment blocks in the candidate set into the focusing parameter determination model. Exemplary second arrangement information corresponding to a possible arrangement of the treatment block in a candidate set includes a location, an angle with respect to the reference axis, etc., of each treatment block corresponding to the possible arrangement. In some embodiments, the processing device 140 may determine the possible arrangements of the treatment blocks in the candidate set based on the attribute information (e.g., the shape, the size, the position, etc.) of the target region of the target region. For each possible arrangement, the inner surfaces of the treatment blocks after the treatment blocks are assembled into the therapeutic ultrasound probe conform to the shape of the target region.

In some embodiments, the processing device 140 may obtain the focusing parameter determination model from one or more components of the therapeutic ultrasound system 100 (e.g., the storage device 150, the terminals(s) 130) or an external source via a network (e.g., the network 120). For example, the focusing parameter determination model may be previously trained by a computing device (e.g., the processing device 140), and stored in a storage device (e.g., the storage device 150) of the therapeutic ultrasound system 100. The processing device 140 may access the storage device and retrieve the focusing parameter determination model.

In some embodiments, the focusing parameter determination model may be generated by training a preliminary model based on a plurality of training samples. Each training sample may include sample arrangement information of ultrasonic transducers in each sample treatment block in a sample set and one or more reference focusing parameters, wherein the one or more reference focusing parameters can be used as a ground truth (also referred to as a label) for model training. In some embodiments, each training sample may further include sample second arrangement information corresponding to a possible arrangement of the sample treatment blocks in the sample set. In some embodiments, the one or more reference focusing parameters may be determined by a user or may be automatically determined by a training device.

The preliminary model may include one or more model parameters, such as the number (or count) of layers, the number (or count) of nodes, a loss function, or the like, or any combination thereof. Before training, the preliminary model may have one or more initial parameter values of the model parameter(s).

The training of the preliminary model may include one or more iterations to iteratively update the model parameters of the preliminary model based on the training sample(s) until a termination condition is satisfied in a certain iteration. Exemplary termination conditions may be that the value of a loss function obtained in the certain iteration is less than a threshold value, that a certain count of iterations has been performed, that the loss function converges such that the difference of the values of the loss function obtained in a previous iteration and the current iteration is within a threshold value, etc. The loss function may be used to measure a discrepancy between one or more focusing parameters predicted by the preliminary model in an iteration and the one or more reference focusing parameters. For example, the sample arrangement information of ultrasonic transducers and sample second arrangement information of each training sample may be inputted into the preliminary model, and the preliminary model may output one or more predicted focusing parameters. The loss function may be used to measure a difference between the one or more predicted focusing parameters and the one or more reference focusing parameters of each training sample. Exemplary loss functions may include a focal loss function, a log loss function, a cross-entropy loss, a Dice ratio, or the like. If the termination condition is not satisfied in the current iteration, the processing device 140 may further update the preliminary model to be used in a next iteration according to, for example, a backpropagation algorithm. If the termination condition is satisfied in the current iteration, the processing device 140 may designate the preliminary model in the current iteration as the focusing parameter determination model.

In 630, the processing device 140 (e.g., the selecting module 420) may determine a target set from the candidate sets based on the one or more focusing parameters of each candidate set and the attribute information of the target region.

In some embodiments, for each candidate set, the processing device 140 determines a focusing accuracy of the candidate set based on the one or more focusing parameters of the candidate set and the attribute information, and selects the candidate set with the highest focusing accuracy as the target set. Exemplary attribute information of the target region may include a location, a size, a shape, etc. of the target region, information relating to a lesion in the target region, or the like, or any combination thereof.

The focusing accuracy of a candidate set reflects whether ultrasonic signals emitted by the treatment blocks in the candidate set can accurately focus on the target region or a lesion region in the target region. For example, the processing device 140 determines the focusing accuracy based on whether the focusing position is located on the target region, the focusing size, and a difference between the focusing intensity and a preset focusing intensity corresponding to the target region. Specifically, if the focusing position (e.g., a central position of the focus) is located on the target region, the focusing accuracy is relatively large. The smaller the focusing size, the higher the focusing accuracy. The smaller the difference between the focusing intensity and the preset focusing intensity corresponding to the target region is, the higher the focusing accuracy.

In some embodiments, as described in connection with operation 620, the arrangement of the treatment blocks in each candidate set is also considered, and multiple sets of focusing parameters corresponding to different possible arrangements of the treatment blocks in each candidate set are determined. In such cases, for each candidate set, the processing device 140 determines focusing accuracies corresponding to the multiple sets of focusing parameters of the candidate set, and further determines a candidate highest focusing accuracy from the focusing accuracies. Then, the processing device 140 determines the highest accuracy among the candidate highest focusing accuracies corresponding to the candidate sets, and determines the candidate set corresponding to the highest accuracy as the target set.

For example, FIG. 7 is a schematic diagram illustrating an exemplary process 700 for determining a target set according to some embodiments of the present disclosure. As shown in FIG. 7, the processing device 140 determines candidate sets 710-750. For each of the candidate sets 710-750, the processing device 140 determines focusing accuracies corresponding to the multiple sets of focusing parameters of the candidate set, and further determines a candidate highest focusing accuracy from the focusing accuracies. Then, the processing device 140 determines the candidate set 740 with the highest accuracy among the candidate highest focusing accuracies corresponding to the candidate sets 710-750, and designates the candidate set 740 as the target set.

In 640, the processing device 140 (e.g., the selecting module 420) may designate the treatment blocks in the target set as the one or more first treatment blocks.

In some embodiments, the processing device 140 may further determine a target arrangement of the first treatment block(s) in the therapeutic ultrasound probe during the treatment to improve the conformity of the therapeutic ultrasound probe to the target region. For example, if the target set is determined by the process 700, the processing device 140 determines the possible arrangement of the treatment blocks in the target set corresponding to candidate highest focusing accuracy as the target arrangement of the treatment blocks in the target set. The one or more first treatment blocks are assembled into the therapeutic ultrasound probe according to the target arrangement, and then the assembled the therapeutic ultrasound probe is used to treat the target region of the target region. In this way, the focusing accuracy of the ultrasonic signals may be greatly improved, thereby improving the effect of the treatment of the target region.

As another example, when the target set is determined, if the arrangement of the treatment blocks in each candidate set is not considered, the processing device 140 determines possible arrangements of the one or more first treatment blocks in the therapeutic ultrasound probe during the treatment. For each of the possible arrangements, the processing device 140 determines one or more focusing parameters of the one or more first treatment blocks when the one or more first treatment blocks have the possible arrangement in a similar manner as described in operation 620. Further, the processing device 140 determines the target arrangement of the one or more first treatment blocks based on the one or more focusing parameters corresponding to each possible arrangement and attribute information of the target region. Specifically, for each possible arrangement, the processing device 140 determines a focusing accuracy corresponding to the possible arrangement based on the one or more focusing parameters corresponding to the possible arrangement and the attribute information. Further, the processing device 140 determines the possible arrangement corresponding to the highest focusing accuracy as the target arrangement.

In some embodiments, as described FIGS. 2A and 2B, at least one ultrasonic transducer array 1112 of the therapeutic ultrasound probe 111 may be movable and/or detachable. When at least one ultrasonic transducer array 1112 in the one or more first treatment blocks may be movable, the processing device 140 may be determine position information of the at least one ultrasonic transducer array 1112 based on attribute information of the target region of the target subject. Specifically, for each first treatment block, the processing device 140 determines a moving range of the at least one ultrasonic transducer array 1112 in the first treatment block. The processing device 140 determines multiple possible arrangements of the at least one ultrasonic transducer array 1112 in the moving range. Further, for each possible arrangement of the at least one ultrasonic transducer array 1112, the processing device 140 determines one or more focusing parameters of the first treatment block(s), and determines a focusing accuracy of the first treatment block(s) based on the one or more focusing parameters and the attribute information of the target region. Then, the processing device 140 determines the possible arrangement with the highest focusing accuracy, and determine the position information of the at least one ultrasonic transducer array 1112 according to the possible arrangement. In this way, the focusing accuracy of the ultrasonic signals for the treatment of the target region may be further improved, thereby further improving the effect of the treatment of the target region.

Figure 8:
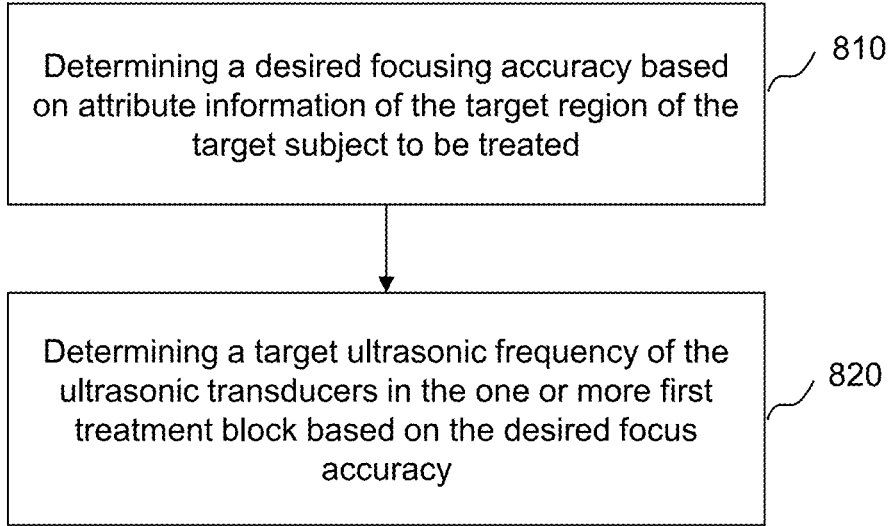
FIG. 8 is a flowchart illustrating an exemplary process for determining a target ultrasonic frequency for a treatment of a target region of a target subject according to some embodiments of the present disclosure.

FIG. 8 is a flowchart illustrating an exemplary process 800 for determining a target ultrasonic frequency for a treatment of a target region of a target subject according to some embodiments of the present disclosure. In some embodiments, when one or more first treatment blocks of the therapeutic ultrasound probe 111 are used for the treatment of the target region and the ultrasonic frequencies of the ultrasonic transducers in the one or more first treatment blocks are different or adjustable, process 800 may be performed.

In 810, the processing device 140 (e.g., the determination module 410) may determine a desired focusing accuracy based on attribute information of the target region of the target subject to be treated.

As used herein, the desired focusing accuracy refers to an appropriate focusing accuracy for the target region.

As described elsewhere in the present disclosure, exemplary attribute information of the target region may include a location, a size (e.g., a minimum width), a shape, etc. of the target region, information relating to a lesion in the target region, or the like, or any combination thereof.

The processing device 140 may determine the desired focusing accuracy based on the attribute information of the target region, ultrasonic frequencies, arrangement information, etc., of the ultrasonic transducers in the one or more first treatment blocks, a tolerable error of the desired focusing accuracy, or the like, or any combination thereof. For example, when the size of the target region is relatively large, the desired focusing accuracy is relatively small, such as 80%. As another example, when the shape of the target region is irregular, the desired focusing accuracy is relatively small. As still another example, when the tolerable error of the desired focusing accuracy is relatively large, the desired focusing accuracy is relatively small.

In 820, the processing device 140 (e.g., the determination module 410) may determine a target ultrasonic frequency of the ultrasonic transducers in the one or more first treatment blocks based on the desired focusing accuracy.

As used herein, the target ultrasonic frequency refers to an ultrasonic frequency for the treatment of the target region of the target subject. That is, when the one or more first treatment blocks are used to the treatment, the ultrasonic transducers in the one or more first treatment blocks emit ultrasonic signals with the target ultrasonic frequency. For example, a first portion of the ultrasonic transducers in the one or more first treatment blocks is able to emit ultrasonic signals with the ultrasonic frequency of f1, and a second portion of the ultrasonic transducers in the one or more first treatment blocks is able to emit ultrasonic signals with the ultrasonic frequency of f2. If the target ultrasonic frequency is f1, the first portion of the ultrasonic transducers are used to be connected with ultrasonic channels.

In some embodiments, the processing device 140 determines the target ultrasonic frequency based on the desired focusing accuracy and ultrasonic wavelengths of the ultrasonic signals emitted by the ultrasonic transducers according to an existing Equation.

In some embodiments, the ultrasonic frequency for treatment is relatively low, and the ultrasonic frequency for imaging is relatively high. Therefore, the ultrasonic transducers with relatively low ultrasonic frequencies may be used for ultrasonic treatment, and the ultrasonic transducers with relatively high frequencies may be used for ultrasonic imaging, and the ultrasonic imaging may be used to monitor the ultrasonic treatment.

According to the process 800 of the present disclosure, the target ultrasonic frequency of the ultrasonic transducers determined based on the desired focusing accuracy is more suitable for the treatment of the target region, thereby improving the treatment effect.

It should be noted that the processes 500, 600, and 800 and the descriptions thereof are provided for the purposes of illustration, and not intended to limit the scope of the present disclosure. For persons having ordinary skills in the art, various modifications and changes in the forms and details of the application of the above method and system may occur without departing from the principles of the present disclosure. However, those variations and modifications also fall within the scope of the present disclosure. For example, the operations of the illustrated processes 500, 600, and 800 are intended to be illustrative. In some embodiments, the processes 500, 600, and 800 may be accomplished with one or more additional operations not described, and/or without one or more of the operations discussed. Additionally, the order in which the operations of the processes 500, 600, and 800 and regarding descriptions are not intended to be limiting.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "module," "unit," "component," "device," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an subject oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate a certain variation (e.g., ±1%, ±5%, ±10%, or ±20%) of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable. In some embodiments, a classification condition used in classification or determination is provided for illustration purposes and modified according to different situations. For example, a classification condition that "a value is greater than the threshold value" may further include or exclude a condition that "the probability value is equal to the threshold value."

What is claimed is:

1. A therapeutic ultrasound system, comprising
a therapeutic ultrasound probe, wherein the therapeutic ultrasound probe is assembled from treatment blocks each of which includes one or more ultrasonic transducer arrays, each of the one or more ultrasonic transducer arrays including one or more ultrasonic transducers, and
each of the treatment blocks is movable to rotate around a reference axis and adjust an angle with respect to the reference axis;
an inner surface of the therapeutic ultrasound probe is an axisymmetric surface or a portion of the axisymmetric surface, and
wherein the therapeutic ultrasound probe is used in combination with a first count of ultrasound channels, and the therapeutic ultrasound system further comprises a processing device configured to:
for each of the treatment blocks, determine a third count of ultrasound channels that are used to be connected to the treatment block;
determining, from the treatment blocks, one or more first treatment blocks such that a second count is to or smaller than the first counts wherein the one or more first treatment blocks are used for a treatment to be performed on a target region of a target subject and the second count is a sum of the third counts corresponding the one or more first treatment blocks; and
causing one or more ultrasonic transducers in the one or more first treatment blocks to emit ultrasonic signals toward the target region;
wherein the processing device is further configured to:
determine possible arrangements of the one or more first treatment blocks in the therapeutic ultrasound probe during a treatment to be performed on a target region of a target subject, wherein the possible arrangements of the one or more first treatment
blocks correspond to different positions and angles for assembling the one or more first treatment blocks;
for each of the possible arrangements, determine one or more focusing parameters of the one or more first treatment blocks when the one or more first treatment blocks have the possible arrangement;
determine a target arrangement of the one or more first treatment blocks based on the one or more focusing parameters corresponding to each possible arrangement and attribute information of the target region;

the reference axis is a symmetry axis of the axisymmetric surface.

2. The therapeutic ultrasound system of claim 1, the treatment blocks are detachable from the therapeutic ultrasound probe.

3. The therapeutic ultrasound system of claim 1, wherein the inner surface of the therapeutic ultrasound probe is a concave surface.

4. The therapeutic ultrasound system of claim 1, wherein one or more second treatment blocks other than the one or more first treatment blocks are removed from the therapeutic ultrasound probe.

5. The therapeutic ultrasound device of claim 1, wherein the third counts corresponding to the treatment blocks are the same, and the processing device is configured to select the one or more first treatment blocks from the treatment blocks by:
determining a fourth count of the one or more first treatment blocks based on the first count and the third count;
selecting a portion of the treatment blocks as the one or more first treatment blocks, the count of the selected portion of the treatment blocks being equal to the fourth count.

6. The therapeutic ultrasound system of claim 5, wherein the fourth count is determined based on a ratio of the first count to the third count.

7. The therapeutic ultrasound system of claim 5, wherein the portion of the treatment blocks are selected from the treatment blocks further based on attribute information of a target region of a target subject to be treated.

8. The therapeutic ultrasound system of claim 7, wherein the ultrasonic transducers of different treatment blocks have different arrangements, and the portion of the treatment blocks are selected from the treatment blocks by:
determining candidate sets of treatment blocks, the count of treatment blocks in each candidate set being equal to the fourth count;
for each of the candidate sets, determining one or more focusing parameters of the candidate set based on arrangement information of the ultrasonic transducers in each treatment block in the candidate set;
determining a target set from the candidate sets based on the one or more focusing parameters of each candidate set and the attribute information of the target region; and
designating the treatment blocks in the target set as the portion of the treatment blocks.

9. The therapeutic ultrasound system of claim 1, wherein the third counts corresponding to at least two of the treatment blocks are different,
the processing device is configured to select the one or more first treatment blocks from the treatment blocks by:
determining one or more candidate sets of treatment blocks based on the third count corresponding to each treatment block, wherein a sum of the third counts corresponding to the treatment blocks in each candidate set is smaller than the first count, and a difference between the sum and the first count is not greater than a threshold value; and
selecting the one or more first treatment blocks based on the one or more candidate sets.

10. The therapeutic ultrasound system of claim 9, wherein the one or more candidate sets include multiple candidate sets, the selecting the one or more first treatment blocks based on the one or more candidate sets comprises:

determining a target set from the candidate sets based on attribute information of a target region of a target subject to be treated; and designating one or more treatment blocks in the target set as the one or more first treatment blocks.

11. The therapeutic ultrasound system of claim 1, wherein at least one of the treatment blocks includes one or more non-treatment regions that are detachable, and the one or more non-treatment regions include one or more ultrasonic transducer arrays used for monitoring a treatment process of a target region.

12. The therapeutic ultrasound system of claim 1, wherein at least one ultrasonic transducer array of the therapeutic ultrasound probe is detachable.

13. The therapeutic ultrasound system of claim 1, wherein each of the treatment blocks includes multiple ultrasonic transducer arrays.

14. The therapeutic ultrasound system of claim 1, wherein sizes of the treatment blocks are different.

15. The therapeutic ultrasound system of claim 1, wherein the therapeutic ultrasound probe further includes one or more non-treatment blocks designed to use in conjunction with the treatment blocks for assembling the therapeutic ultrasound probe, each of the one or more non-treatment blocks does not include any ultrasound transducer arrays.

16. The therapeutic ultrasound system of claim 8, wherein the one or more focusing parameters of each candidate set include multiple sets of focusing parameters corresponding to different possible arrangements of the treatment blocks in the candidate set, and the target set is determined by:

for each candidate set, determining focusing accuracies corresponding to the multiple sets of focusing parameters; and determining a candidate highest focusing accuracy from the focusing accuracies;

determining the highest accuracy among the candidate highest focusing accuracies corresponding to the candidate sets; and determining the candidate set corresponding to the highest accuracy as the target set.

17. A method for treating a target subject using a therapeutic ultrasound system, the therapeutic ultrasound system comprising a therapeutic ultrasound probe, wherein the therapeutic ultrasound probe comprises treatment blocks each of which includes one or more ultrasonic transducer arrays, each of the one or more ultrasonic transducer arrays including one or more ultrasonic transducers, and the treatment blocks are movable to rotate around a reference axis and/or adjust an angle with respect to the reference axis and the therapeutic ultrasound probe is used in combination with a first count of ultrasound channels, wherein the method is implemented on a computing device having at least one processor and at least one storage device and comprises:

for each of the treatment blocks, determining a third count of ultrasound channels that are used to be connected to the treatment block:

determining, from the treatment blocks, one or more first treatment block such that a second count is equal to or smaller than the first count, wherein the one or more first treatment blocks are used for a treatment to be performed on a target region of the target subject, and the second count is a sum of the third counts corresponding the one or more first treatment blocks; and wherein the processer is further configured to:

determine possible arrangements of the one or more first treatment blocks in the therapeutic ultrasound probe during a treatment to be performed on a target region of a target subject, wherein the possible arrangements of the one or more first treatment blocks correspond to different positions and angles for assembling the one or more first treatment blocks;

for each of the possible arrangements, determine one or more focusing parameters of the one or more first treatment blocks when the one or more first treatment blocks have the possible arrangement;

determine a target arrangement of the one or more first treatment blocks based on the one or more focusing parameters corresponding to each possible arrangement and attribute information of the target region;

causing one or more ultrasonic transducers in the one or more first treatment blocks to emit ultrasonic signals toward the target region.

18. A non-transitory computer readable medium, comprising at least one set of instructions for treating a target subject using a therapeutic ultrasound system, the therapeutic ultrasound system comprising a therapeutic ultrasound probe, wherein the therapeutic ultrasound probe comprises treatment blocks each of which includes one or more ultrasonic transducer arrays, each of the one or more ultrasonic transducer arrays including one or more ultrasonic transducers, the treatment blocks are movable to rotate around a reference axis and/or adjust an angle with respect to the reference axis, an inner surface of the therapeutic ultrasound probe is an axisymmetric surface or a portion of the axisymmetric surface, and the reference axis is a symmetry axis of the axisymmetric surface;

wherein the therapeutic ultrasound probe is used in combination with a first count of ultrasound channels, wherein the method is implemented on a computing device having at least one processor and at least one storage device and comprises executing instruction for:

determining, from the treatment blocks, one or more first treatment blocks of the therapeutic ultrasound probe are used for a treatment to be performed on a target region of the target subject;

for each of the treatment blocks, determine a third count of ultrasound channels that are used to be connected to the treatment block;

determining, from the treatment blocks, one or more first treatment blocks such that a second count is to or smaller than the first counts wherein the one or more first treatment blocks are used for a treatment to be performed on a target region of a target subject and the second count is a sum of the third counts corresponding the one or more first treatment blocks; and wherein the processer is further configured to:

determine possible arrangements of the one or more first treatment blocks in the therapeutic ultrasound probe during a treatment to be performed on a target region of a target subject, wherein the possible arrangements of the one or more first treatment blocks correspond to different positions and angles for assembling the one or more first treatment blocks;

for each of the possible arrangements, determine one or more focusing parameters of the one or more first treatment blocks when the one or more first treatment blocks have the possible arrangement;

determine a target arrangement of the one or more first treatment blocks based on the one or more focusing parameters corresponding to each possible arrangement
and attribute information of the target region; and
causing one or more ultrasonic transducers in the one or
more first treatment blocks to emit ultrasonic signals
toward the target region.

* * * * *